United States Patent
Fourtillan et al.

(10) Patent No.: US 6,335,346 B1
(45) Date of Patent: Jan. 1, 2002

(54) PYRROLO-(3,4-B)QUINOLINE DERIVATIVES, METHOD FOR THE PRODUCTION AND USE THEREOF AS A MEDICAMENT

(75) Inventors: Jean-Bernard Fourtillan; Marianne Fourtillan, both of Poitiers; Jean-Claude Jacquesy, Buxerolles; Omar Karam, Saint-Benoît; Fabien Zunino, Buxerolles; Marie-Paule Jouannetaud, Poitiers, all of (FR)

(73) Assignees: MACEF, Migne Auxances; Laboratoires Besins Iscovesco, Paris, both of (FR)

( * ) Notice: Subject to any disclaimer, the term of this patent is extended or adjusted under 35 U.S.C. 154(b) by 0 days.

(21) Appl. No.: 09/720,593

(22) PCT Filed: Apr. 27, 2000

(86) PCT No.: PCT/FR00/01123

§ 371 Date: Dec. 26, 2000

§ 102(e) Date: Dec. 26, 2000

(87) PCT Pub. No.: WO00/64897

PCT Pub. Date: Nov. 2, 2000

(30) Foreign Application Priority Data

Apr. 27, 1999 (FR) .................................. 99 05302

(51) Int. Cl.[7] .................. A61K 31/437; A61K 31/4375; A61P 25/20; C07D 471/04; C07D 471/14
(52) U.S. Cl. ............................ 514/285; 514/292; 546/70; 546/84
(58) Field of Search ........................ 546/70, 84; 514/285, 514/292

(56) References Cited

U.S. PATENT DOCUMENTS 4,943,579 A 7/1990 Vishouvajjala et al.

FOREIGN PATENT DOCUMENTS

| CA | 2157128 | 8/1995 |
|---|---|---|
| EP | 0 296 612 A1 | 12/1988 |
| EP | 0 296 612 B1 | 12/1988 |
| EP | 0 556 585 A2 | 8/1993 |
| EP | 0 685 481 A2 | 12/1995 |
| EP | 0 685 481 B1 | 12/1995 |
| WO | WO/96/08490 A1 | 3/1996 |
| WO | WO/97/43290 | 11/1997 |

OTHER PUBLICATIONS

International Search Report for PCT/FR00/01123.
Pendrak et al.; Synthesis and Anti–HSV Activity of Methylenedioxy Mappicine Ketone Analogs; *J. Org. Chem.* 1995, 60:2912–2915.
Sugasawa et al.; A Total Synthesis of dl–Campotothecin; *Tetrahedron Letters* 1972, 50:5109–5112.
Fortunak et al.; Preparation of Mappicine Ketones from Camptothecins: Chemistry of the Camptothecin E Ring; *Tetrahedron Letters* 1994, 35:5763–5764.
Curran et al.; Tandem Radical Reactions of Isonitriles with 2–Pyridonyl and Other Aryl Radicals: Scope and Limitations, and a First Generation Synthesis of (±)–Campotothecin; *Tetrahedron* 1996, 52:11385–11404.
Fortunak et al.; Novel Synthesis of Camptothecin Alkaloids, Part 2.[1] Concise Synthesis of (S)–Camptothecins; *Tetrahedron Letters* 1996, 32:5683–5686.
Comins et al.; Concise Synthesis of Mappicine Ketone and (±)–Mappicine; *J. Org. Chem.* 1996, 61:9623–9624.
Meyers et al.; A Total Synthesis of Camptothecin and Deethyldeoxycamptothecin; *J. Org. Chem.* 1973, 38(11):1974–1982.
Danishefsky et al.; Isocamptothecin; *Tetrahedron Letters* 1973, 27:2521–2524.
Stork et al.; The Total Synthesis of dl–Camptothecin; *J. Amer. Chem. Soc.* 1971, 4074–4075.
Rigby et al.; Vinyl Isocyanates in Alkaloid Synthesis. Camptothecin Model Studies; *Tetrahedron Letters* 1997, 38(28):4969–4972.
Kitajima et al.; Isolation and Partial Synthesis of 3(R)– and 3(S)–Deoxypumiloside; Structural Revision of the Key Metabolite from the Camptothecin Producing Plant *Ophiorrhiza pumila* 1997, 38(24):4255–4258.
Bock et al.; Die Biogenetisch Orientierte Totalsynthese von DL–Camptothecin und 7–Chlor–Camptothecin; *Chem. Ber.* 1972, 105:2126–2142.
Murata et al.; Synthesis of Functionalized Heteroaromatics: Application to Formal Total Synthesis of Camptothecin; *SYNLETT* 1996, 298–300.
Fortunak et al.; Novel Syntheses of Camptothecin Alkaloids, Part I. Intramolecular [4+2] Cycloadditions of N–arylimidates and 4H–3,1–benzoxazin–4–ones as 2–Aza–1, 3–Dienes; *Tetrahedron Letters* 1996, 37(32):5679–5682.
Warneke et al.; Die autoxydative Indol–Chinolon–Umwandlung eines Camptothecin–Modells; *Chem. Ber.* 1972, 105:2120–2125.

*Primary Examiner*—Evelyn Mei Huang
(74) *Attorney, Agent, or Firm*—Finnegan, Henderson, Farabow, Garrett & Dunner, L.L.P.

(57) ABSTRACT

The invention relates to pyrrolo[3,4-b]quinoline derivatives of general formula (I) wherein X represents an oxygen atom or a sulphur atom. Said derivatives have a hypnotic or sedative effect.

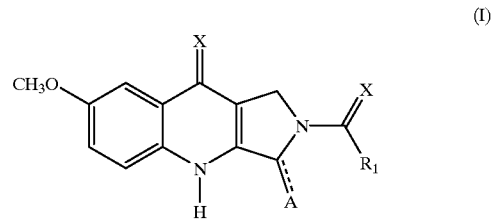

(I)

10 Claims, No Drawings

PYRROLO-(3,4-B)QUINOLINE DERIVATIVES, METHOD FOR THE PRODUCTION AND USE THEREOF AS A MEDICAMENT

This application is the national phase of PCT/FR00/01123, filed Apr. 27, 2000.

The present invention relates to novel pyrrolo[3,4-b) quinoline derivatives of general formula I:

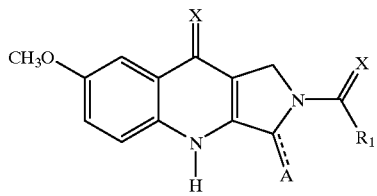

in which X represents an oxygen atom or a sulfur atom,

represents a group of formula:

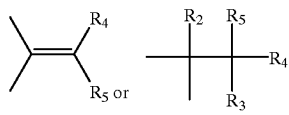

$R_1$ represents a lower alkyl radical containing from one to three carbon atoms, a lower cycloalkyl radical containing from three to six carbon atoms or $R_1$ represents a lower alkyl radical linked to $R_4$ to form a 6-atom ring containing 0, 1 or 2 unsaturations, $R_2$, $R_3$, $R_4$ and $R_5$ represent, independently of each other, a hydrogen atom, a lower alkyl group containing from one to three carbon atoms, a lower cycloalkyl group containing from three to six carbon atoms or a phenyl group, the corresponding racemic mixtures, as well as the pure enantiomers thereof or mixtures thereof in all proportions and the pharmaceutically acceptable salts thereof.

The term "lower alkyl" means linear or branched $C_1$–$C_3$ alkyl residues chosen more particularly from methyl, ethyl, n-propyl, isopropyl and cyclopropyl groups.

When the derivatives comprise at least one asymmetric carbon, the present invention relates to the corresponding racemic mixtures, as well as to the pure enantiomers thereof or mixtures thereof in all proportions.

The therapeutically acceptable salts of the derivatives according to the invention are common organic or inorganic salts of the art, the hydrochlorides, tosylates, mesylates and citrates, as well as solvates such as the hydrates or hemihydrates of the compounds of general formula I.

The present invention more particularly relates to the derivatives of general formula I for which X preferably represents an oxygen atom or a sulfur atom.

Preferentially, $R_1$ advantageously represents a lower alkyl radical, optionally linked to $R_4$ to form a 6-atom ring, or a methyl, ethyl, n-propyl, isopropyl or cyclopropyl group.

Various pyrroloquinoline derivatives have been described in the prior art as synthetic intermediates by:

I. Pendrak, R. Winttrock, W. D. Kingsbury, J. Org. Chem, Vol. 60, No. 9, 1995, pages 2912–2915. T. Sugasowa, T. Toyoda, K. Saskura, Tetrahedron. Lett, No. 50, pages 5109–5112; J. M. D. Fortunak, A. R. Mastrocola, M. Mellinger, J. L. Wood, Tetrahedron. Lett; Vol. 35, No. 32, pages 5763–5764; D. P. Curran, H. Liu, H. Josien, Tetrahedron Lett, Vol. 52, No. 35, pages 11385–11404; J. M. D. Fortunak, A. R. Mastrocola, M. Mellinger, N. J. Sisti, J. L. Wood, Z. P. Zhung Tetrahedron. Lett; Vol. 37, No. 32, pages 5683–5686; D. L. Comins, J. K. Seha, J. Org. Chem, Vol. 61, No. 26, pages 9623–9624; A. I. Meyers et al., J. Org. Chem, Vol. 38, No. 8, 1993; S. Danishefsky, R. Volkmann, S. B. Horwitz, Tetrahedron Lett, No. 27, 1973, pages 2521, 2524; G. Stork, A. G. Schultz, J. Am. Chem. Soc, Vol. 93, No. 16, 1971; J. H. Rigby, D. M. Danca Tetrahedron Lett, Vol. 38, No. 28, 1997, pages 4969, 4972; M. Kitajima, S. Mosomoto, H. Takayama, N. Aimi, Tetrahedron. Lett, Vol. 38, No. 24, 1997, pages 4255–4258; M. Boch, T. Korth, J. M. Nelke, D. Pike, H. Radunz, Chem. Ber, 105, 1992, pages 2126–2142; M. Naoko, S. Takumchi, K. Yoshinori, S. Tako, Synlett, 1997, pages 298–300; J. M. D. Fortunak, A. R. Mastrocola, M. Mellinger, N. J. Sisti, J. L. Wood, Z. P. Zhung Tetrahedron. Lett; Vol. 37, No. 32, pages 5679–5682; I. Pendrak, R. Winttrock, W. D. Kingsbury, J. Org. Chem., Vol. 60, No. 9, 1995, pages 2912–2915; J. Warneke, E. Winterfeldt, Chem. Ber, 105, 1972, pages 2120–2125.

T. Yaegashi et al. (CA. 157128, 960307); S. Sawada et al. (EP 296612, 881228); B. R. Vishnuvajjala et al. (U.S. Pat. No. 4,943,579, 900724); H. Akimoto et al. (EP 556585, 930825); E. Bombardelli et al. (EP 685481, 951206) and E. Bombardelli, L. Verotta (PCT INT Appl. WO 97 43, 290) have disclosed pyrroloquinoline derivatives which have therapeutic activity, although this activity is not hypnotic or sedative activity.

The present invention relates to the pyrrolo[3,4-b] quinoline derivatives of general formula I as defined above.

The derivatives of general formula I, for which X represents an oxygen atom, can be obtained directly by oxidizing the compounds of general formula II

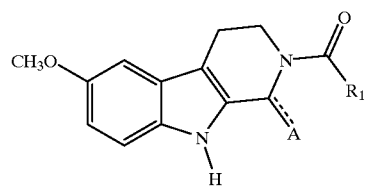

for which $R_1$ and A are defined above, with oxygen in the presence of a base such as sodium hydride or potassium tert-butoxide, or with a periodate.

The sulfur analogs of general formula I (X=S) are obtained from the corresponding oxygen derivatives of formula I (X=O) by the action of Lawesson's reagent, or by the action of phosphorus pentasulfide.

The examples which follow of preparations of derivatives according to the invention illustrate the present invention.

Examples of derivatives of general formula I, for which:

A) X represents an oxygen atom and

represents a group of formula

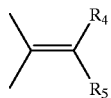

when $R_4$ and $R_5$ each represent a hydrogen atom, are given in Table I below

TABLE I

| Example | $-R_1$ |
|---|---|
| 1 | $-CH_3$ |
| 2 | $-(CH_2)_2-CH_3$ |
| 3 |  | when $R_1$ and $R_4$ are linked to form a ring corresponding to formula III

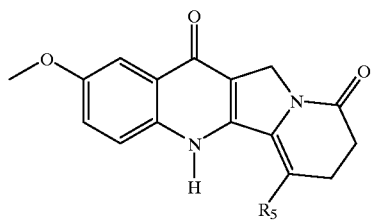

III are given in Table II below

TABLE II

| Example | $-R_5$ |
|---|---|
| 4 | $-CH_2-CH_3$ |
| 5 | 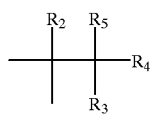 |

B) X represents an oxygen or sulfur atom, and

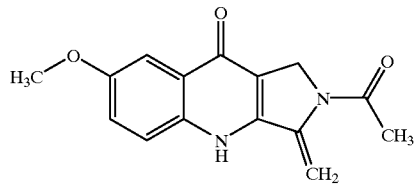

represents a divalent radical of formula when $R_3$, $R_4$ and $R_5$ each represent a hydrogen atom and $R_1$ represents a methyl radical are given in Table III below

TABLE III

| Example | X | $-R_2$ |
|---|---|---|
| 6 | O | $-H$ |
| 7 | S | $-H$ |
| 8 | O | $-CH_3$ | when $R_1$ and $R_4$ are linked to form a ring corresponding to formula IV, $R_2$ represents a hydrogen atom and X represents an oxygen atom

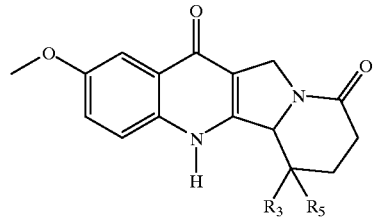

IV are given in Table IV below

TABLE IV

| Example | $R_3$ | $-R_5$ |
|---|---|---|
| 9 | H | $-CH_2-CH_3$ |
| 10 | $-CH_2-CH_3$ | $-CH_2-CH_3$ |

EXAMPLE 1

Formula: $C_{15}H_{14}N_2O_3$ M=270.28 g.mol$^{-1}$

Structure:

2-Acetyl-7-methoxy-3-methylene-9-oxo-1,3,4,9-tetrahydropyrrolo[3,4-b]quinoline

Preparation:

NaH (1.5 eq; 60% suspension in oil) is added to a solution of 1-methylene-2-acetyl-6-methoxy-1,2,3,4-tetrahydro-β-carboline (1 g; 3.9 mmol) in DMF (5 ml). The mixture is stirred under an oxygen atmosphere overnight. The DMF is then distilled off under reduced pressure. The crude product is washed successively with ethyl acetate, methanol and then ether. After drying, 2-acetyl-7-methoxy-3-methylene-9-oxo-1,3,4,9-tetrahydropyrrolo[3,4-b]quinoline is obtained.

$^1$H NMR: MeOH-d$_4$: 2.30 (s, 3H, CH$_3$CO—Nb); 3.89 (s, 3H, CH$_3$O); 4.87 (s, 2H, CH$_2$—Nb); 5.69 (s, 1H, vinyl H); 6.03 (s, 1H, vinyl H); 7.14 (dd, 1H, J$_1$=9 Hz, J$_2$=3 Hz, H-6); 7.68 (m, 2H, H-5 and H-8); 8.53 (broad s, 1H, NH). Mass spectrum: m/z: 270 (M$^+$), 228 (100), 213, 199, 184, 155.

EXAMPLE 2

Formula: $C_{17}H_{18}N_2O_3$ M=298.34 g.mol$^{-1}$
Structure:

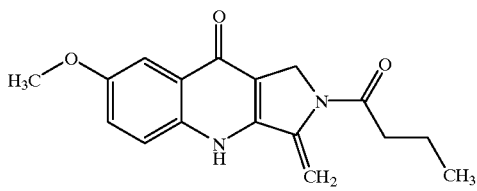

2-Butyryl-7-methoxy-3-methylene-9-oxo-1,3,4,9-tetrahydropyrrolo[3,4-b]quinoline Preparation:

NaH (1.5 eq; 60% suspension in oil) is added to a solution of 1-methylene-2-butyryl-6-methoxy-1,2,3,4-tetrahydro-β-carboline (160 mg; 0.6 mmol) in DMF (3 ml). The mixture is stirred under an oxygen atmosphere for 6 hours. The DMF is then distilled off under reduced pressure. The crude product is washed several times with ethyl acetate. After filtration and drying, 2-butyryl-7-methoxy-3-methylene-9-oxo-1,3,4,9-tetrahydropyrrolo[3,4-b]quinoline is obtained (yield=40%).

$^1$H NMR: MeOH-d$_4$: 0.9 and 1.0 (2t, 3H, J=7.2 Hz, CH$_3$); 1.6 and 1.8 (2q, 2H, J=7.2 Hz, CH$_2$CH$_3$); 2.1 and 2.5 (2t, 2H, J=7.2 Hz, COCH$_2$CH$_2$); 3.89 (s, 3H, OCH$_3$); 4.87 (s, 2H, H-1); 5.68 (s, 1H, vinyl H); 6.07 (s, 1H, vinyl H); 7.14 (dd, 1H, J$_1$=9 Hz, J$_2$=3 Hz, H-6); 7.42 (d, 1H, J=3 Hz, H-8); 7.68 (d, J 9 Hz, H-5); 8.52 (broad s, 1H, NH). Mass spectrum: m/z: 298 (M$^+$), 228 (100), 213, 199, 184.

EXAMPLE 3

Formula: $C_{17}H_{16}N_2O_3$ M=296.32 g.mol$^{-1}$
Structure:

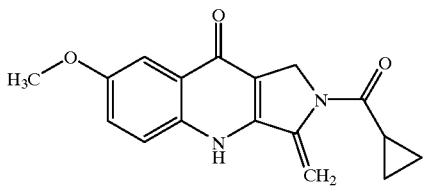

2-Cyclopropylcarbonyl-7-methoxy-3-methylene-9-oxo-1,3,4,9-tetrahydropyrrolo[3,4-b]quinoline Preparation:

NaH (1.2 eq; 60% suspension in oil) is added to a solution of 1-methylene-2-cyclopropylcarbonyl-6-methoxy-1,2,3,4-tetrahydro-β-carboline (500 mg; 1.7 mmol) in DMF (5 ml). The mixture is stirred under an oxygen atmosphere for 48 hours, further NaH (1.1 eq) is then added and stirring is continued overnight. The DMF is then distilled off under reduced pressure. The crude product is taken up in water and then filtered off. Saturated NH$_4$Cl solution is added to the aqueous phase. The mixture is stirred for 30 minutes. The precipitate is filtered off and then washed successively with water, an MeOH/CH$_2$Cl$_2$ mixture (10/90), acetone and then ethyl acetate. After drying, 2-cyclopropylcarbonyl-7-methoxy-3-methylene-9-oxo-1,3,4,9-tetrahydropyrrolo[3,4-b]quinoline is obtained (yield=38%).

$^1$H NMR: CDCl$_3$: 0.97 (m, 2H, cyclopropyl CH$_2$); 1.1 (m, 2H, cyclopropyl CH$_2$); 1.91 (m, H, cyclopropyl CH); 3.90 (s, 3H, OCH$_3$); 5.03 (s, 2H, H-1); 5.43 (s, 1H, vinyl H); 6.19 (s, 1H, vinyl H); 7.30 (d, J=9 Hz, H-8); 7.50 (dd, J$_1$=9 Hz, J$_2$=3 Hz, H-7); 7.67 (d, J=3 Hz, H-5). Mass spectrum: m/z: 296 (M$^+$), 228 (100), 213, 199, 184.

EXAMPLE 4

Formula: $C_{18}H_{18}N_2O_3$ M=310.35 g.mol$^{-1}$
Structure:

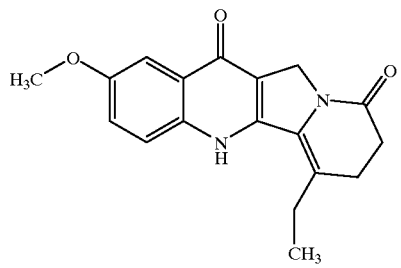

1-Ethyl-9-methoxy-2,3,4,6,7,12-hexahydroindolizino[1,2-b]quinoline-4,7-dione Preparation:

9-Methoxy-1-ethyl-2,3,4,6,7,12-hexahydro-indolo[2,3-a]quinolizin-4-one (500 mg; 1.7 mmol) is dissolved in dimethylformamide (DMF) (45 ml) in a 100 ml round-bottomed flask and potassium tert-butoxide (700 mg; 6.2 mmol) is added. The mixture is stirred under an oxygen atmosphere at room temperature for 48 hours. Water (55 ml) and concentrated hydrochloric acid (15 ml) are then added successively with stirring. The product, 1-ethyl-9-methoxy-2,3,4,6,7,12-hexahydroindolizino[1,2-b]quinoline-4,7-dione, precipitates after recrystallization from an ethanol/chloroform mixture (140 mg; yield=26%).

$^1$H NMR: (CDCl$_3$/CD$_3$OD—70/30): 1.23 (t, 3H, CH$_3$); 2.66 (m, 4H, 2CH$_2$); 2.84 (q, 4H, CH$_2$), 3.97 (s, 3H, CH$_3$O); 4.85 (s, 2H, CH$_2$); 7.47 (d, 1H, ArH); 7.67 (s, 1H, ArH), 8.17 (d, 1H, ArH) Mass spectrum: m/z: 310 (M$^+$100), 295, 281, 267.

EXAMPLE 5

Formula: $C_{23}H_{19}NO_3$ M=357.40 g.mol$^{-1}$
Structure:

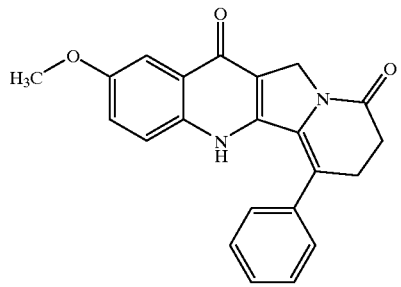

9-Methoxy-1-phenyl-2,3,4,6,7,12-hexahydroindolizino[1,2-b]quinoline-4,7-dione Preparation:

Potassium tert-butoxide (1.75 g; 15 mmol) is added to a solution of 9-methoxy-1-phenyl-2,3,4,6,7,12-hexahydroindolo[2,3-a]quinolizin-4-one (1,45 g; 40 mmol) in DMF (100 ml). The mixture is stirred under an oxygen atmosphere overnight. After evaporation and purification on a column of silica (eluent: 95/5 chloroform/methanol) and drying, 9-methoxy-1-phenyl-2,3,4,6,7,12-hexahydroindolizino[1,2-b]quinoline-4,7-dione is obtained (200 mg; 13%).

$^1$H NMR: CDCl$_3$-MeOH: 2.70 (d, J=7.1 Hz, 2H); 2.85 (s, 1H), 3.81 (s, 3H, CH$_3$O); 4.77 (s, 2H); 6.70 (d, J=9 Hz; 1H), 7.08 (d, J=8.7 Hz), 7.41 (m, 6H). Mass spectrum: m/z: 358 (M$^+$)(100), 329, 253.

EXAMPLE 6

Formula: C$_{15}$H$_{16}$N$_2$O$_3$ M=272.30 g.mol$^{-1}$
Structure:

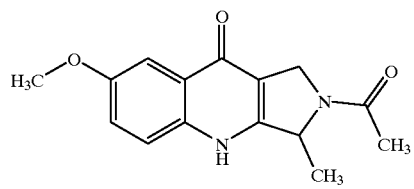

2-Acetyl-7-methoxy-3-methyl-9-oxo-1,3,4,9-tetrahydropyrrolo[3,4-b]quinoline

Preparation:

NaH (1.2 eq; 60% suspension in oil) is added to a solution of 1-methyl-2-acetyl-6-methoxy-1,2,3,4-tetrahydro-β-carboline (1.56 g; 6.0 mmol) in DMF (20 ml). The mixture is stirred under an oxygen atmosphere for 48 hours, further NaH (1.1 eq) is then added and stirring is continued overnight. The DMF is then distilled off under reduced pressure. The crude product is taken up in water and then filtered. Saturated NH$_4$Cl solution is added to the aqueous phase. The mixture is stirred for 30 minutes. The precipitate is filtered off and then washed successively with water, an MeOH/CH$_2$Cl mixture (10/90), acetone and then ethyl acetate. After drying, 2-acetyl-7-methoxy-3-methyl-9-oxo-1,3,4,9-tetrahydropyrrolo[3,4-b]quinoline is obtained (yield=45%).

1H NMR: CDCl$_3$/MeOH-d$_4$ (9/1): 1.54 (d, 3H, J=6.3 Hz, CH$_3$); 2.17 (s, 3H, CH$_3$CO—Nb); 3.90 (s, 3H, CH$_3$O); 4.73 (s, 2H, CH$_2$—Nb); 5.20 (q, 1H, J=6.4 Hz, H-3); 7.24 (dd, 1H, J$_1$=9 Hz, J$_2$=3 Hz, H-6); 7.36 (d, 1H, J=9 Hz, H-5); 7.70 (d, 1H, J=3 Hz, H-8) Mass spectrum: m/z: 272 (M$^+$), 229 (100), 215, 199.

EXAMPLE 7

Formula: C$_{15}$H$_{16}$N$_2$OS$_2$ M=304.42 g.mol$^{-1}$
Structure:

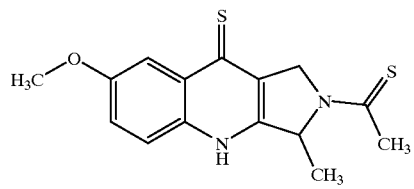

7-Methoxy-3-methyl-2-thioacetyl-9-thioxo-1,3,4,9-tetrahydropyrrolo[3,4-b]quinoline Preparation:

2-Acetyl-7-methoxy-3-methyl-9-oxo-1,3,4,9-tetrahydropyrrolo[3,4-b]quinoline (Example 7) (100 mg; 0.4 mmol) is dissolved in toluene (15 ml), Lawesson's reagent (180 mg; 0.44 mmol) is then added and the mixture is heated at the reflux point of the toluene overnight. After evaporation of the toluene and purification on a silica plate (98.5/1.5 chloroform/methanol), 7-methoxy-3-methyl-2-thioacetyl-9-thioxo-1,3,4,9-tetrahydropyrrolo[3,4-b]quinoline is obtained (20 mg; yield=18%).

$^1$H NMR: (CDCl$_3$/CD$_3$OD—95/5): 1.70 (d, 3H, CH$_3$); 2.69 (s, 3H, CH$_3$CS); 3.94 (s, 3H, CH$_3$O), 4.82 (dd, 2H, CH$_2$); 5.75 (q, 1H, CH); 7.29 (dd, 1H, ArH), 7.42 (d, 1H, ArH), 8.23 (d, 1H, ArH) Mass spectrum: m/z: 314 (M$^+$, 100), 271, 245.

EXAMPLE 8

Formula: C$_{16}$H$_{18}$N$_2$O$_3$ M=286.33 g.mol$^{-1}$
Structure:

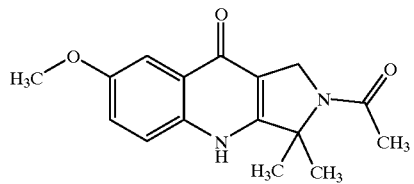

2-Acetyl-3,3-dimethyl-7-methoxy-9-oxo-1,3,4,9-tetrahydropyrrolo[3,4-b]quinoline

Preparation:

Potassium tert-butoxide (269 mg; 2.39 mmol) is added to a solution of 2-acetyl-1,1-dimethyl-6-methoxy-1,2,3,4-tetrahydro-β-carboline (164 mg; 0.60 mmol) in DMF (15 ml). The mixture is stirred under an oxygen atmosphere overnight. A 1/1 ethyl acetate/methanol mixture (10 ml) is then added. After evaporating the solvent and washing the solid, 2-acetyl-3,3-dimethyl-7-methoxy-9-oxo-1,3,4,9-tetrahydropyrrolo[3,4-b]quinoline is obtained (38 mg; 22%)

$^1$H NMR: CDCl$_3$/MeOH-d$_4$ (9/1): 1.87 (s, 6H) ; 2.19 (s, 3H) 3.93 (s, 3H); 7.34 (dd, 1H); 7.59 (d, 1H); 7.70 (d, 1H) Mass spectrum: m/z: 286 (M$^+$), 271, 243, 229 (100), 213.

EXAMPLE 9

Formula: C$_{18}$H$_{20}$N$_2$O$_3$ M=312.36 g.mol$^{-1}$
Structure:

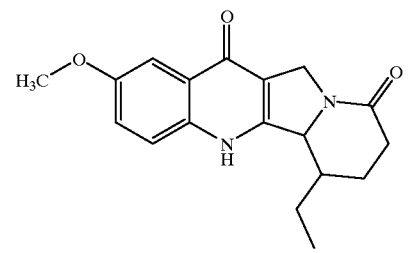

1-Ethyl-9-methoxy-1,2,3,4,6,7,12,12b-octahydroindolizino[1,2-b]quinoline-4,7-dithione Preparation:

Potassium tert-butoxide (1.4 g ; 12.4 mmol) is added to a solution of 9-methoxy-1-ethyl-1,2,3,4,6,7,12,12b- octahydroindolo[2,3-a]quinolizin-4-one (1.0 g; 3.35 mmol) in DMF (90 ml). The mixture is stirred under an oxygen atmosphere overnight. A 1/1 ethyl acetate/methanol mixture (10 ml) is then added. After evaporation and purification on a column of silica (eluent: 95/5 chloroform/methanol), 1-ethyl-9-methoxy-1,2,3,4,6,7,12,12b-octahydroindolizino[1,2-b]quinoline-4,7-dithione is obtained (360 mg; 34%).

$^1$H NMR: CDCl$_3$/MeOH-d$_4$ (9/1): 0.89 (t, 3H, J=7.4 Hz); 1.10 (q, 2H, J=7.4 Hz), 2.07 (m, 2H); 2.44 (m, 3H), 3.90 (s, 3H, CH$_3$O); 4.45 (d, 1H, J=14.8 Hz); 4.90 (d, 1H, J=14.8 Hz); 4.99 (s, 1H), 7.26 (dd, 1H, J$_1$=9 Hz, J$_2$=2.7 Hz); 7.49 (d, 1H, J=9 Hz, H-5); 7.69 (d, 1H, J=2.7 Hz) Mass spectrum: m/z: 312 (M$^{3o}$) (100), 283, 214, 199, 171.

EXAMPLE 10

Formula: C$_{20}$H$_{24}$N$_2$O$_3$ M=340.43 g.mol$^{-1}$
Structure:

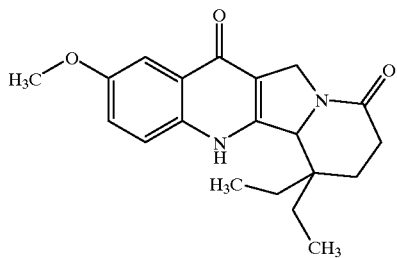

1,1-Diethyl-9-methoxy-1,2,3,4,6,7,12,12b-octahydroindolizino[1,2-b]quinoline-4,7-dithione Preparation:

Potassium tert-butoxide (113 mg; 1.0 mmol) is added to a solution of 9-methoxy-1,1-diethyl-1,2,3,4,6,7,12,12b-octahydroindolo[2,3-a]quinolizin-4-one (80 mg; 0.24 mmol) in DMF (7 ml). The mixture is stirred under an oxygen atmosphere overnight. A 1/1 ethyl acetate/methanol mixture (10 ml) is then added. After evaporation and purification on a column of silica (eluent: 97.5/4.5 chloroform/methanol), 1,1-diethyl-9-methoxy-1,2,3,4,6,7,12,12b-octahydroindolizino[1,2-b]quinoline-4,7-dithione is obtained (31 mg; 37%).

$^1$H NMR: CDCl$_3$/MeOH-d$_4$ (9/1) [lacuna] Mass spectrum: m/z: 340 (M$^+$) 309; 214 (100), 199, 171.

PHARMACOLOGICAL ACTIVITY

1. HYPNOTIC ACTIVITY IN BEAGLE DOGS
(Measurement of the Conscious and Sleeping States)

During each test, the dogs are taken to a recording room in which they are connected to a Schwarzer ED 24 polygraph driven by Brainlab® for Windows® by means of a flexible cable. The dog is then placed in a 0.70×1×0.8 m metal cage in which it stays for 150 minutes.

The test products and the placebo were administered intravenously as a single bolus into the anterior median vein. The recordings are noted in periods of 30 seconds following the five states of vigilance defined by Shelton et al.:

conscious,
drowsy,
light slow-wave sleep,
deep slow-wave sleep, and
paradoxal sleep, by examining the amplitude and frequency of the 2 frontal EEG plots (frontal), the EOG plots (bilateral) and the EMG plots (neck muscles) as follows:

Conscious: The dogs may be standing, sitting or lying down, or moving between these positions. Their eyes are open. This state includes all the episodes of multiple voltage and frequency with muscular activity.

Drowsy: The dogs are lying down with the eyes closed for most of the time. The EEG plots show slow-wave cycles (5–7 Hz) without the appearance of spindles. Large-amplitude synchronous slow waves (4–7 Hz) appear on a background of rapid activity. The EMG tends to be reduced compared with the conscious state.

Light sleep (SL1 or S1): The dogs are lying down in the stretched ventral position or, usually, in an incomplete circle. The relaxation is total. The EEG plots are characterized by K complexes and/or spindles. The amplitude increases.

Deep sleep (SL2 or S2): The dogs are lying down, with relaxed muscles. They remain without reaction to moderate stimulations (by sound). The slow delta waves (<4 Hz) with an amplitude of at least 70 µV constitute at least 20% of a period of 30 seconds.

Paradoxal sleep (PS): The dogs are lying down with the eyes closed and occasionally display rapid contractions of the eyelids and/or myoclonia, in particular of the labial extensor muscles. The EEG plots are of low voltage and varied frequencies. The EOG plots show rapid contractions. The EMG plot is of low amplitude, with the exception of the short-lived clonus. A period is classified as paradoxal sleep only if the preceding period is a period of sleep. The end of a period of paradoxal sleep is determined by the appearance of K complexes or spindles, or by the appearance of EMG activity.

The test compounds are administered intravenously by means of a vehicle having the composition: 50/50 (V/V) PEG-400/water for injectable preparations, as a single bolus of 10 ml per 12 kg of live weight.

The placebo consists of the intravenous administration of the vehicle alone, having the composition: 50/50 (V/V) PEG-400/water for injectable preparations, as a single bolus of 10 ml per 12 kg of live weight.

The distribution of the observation time spent in each of the stages of consciousness and sleep, as well as the latency times for onset of the first stages of each type of sleep, are given in Table I.

The compounds of Examples 4 aind 5 have marked hypnotic power. They induce a sleep characterized by a high proportion of slow waves. The duration of the periods of consciousness is reduced and that of the unconscious phases is increased for each of these two compounds. The latency times for onset of drowsiness, light slow-wave sleep arid deep slow-wave sleep are also reduced.

TABLE I

DURATION OF THE STAGES OF CONSCIOUSNESS AND ONSET LATENCY TIMES (MINUTES)
OBSERVED IN 7 BEAGLE DOGS AFTER INTRAVENOUS ADMINISTRATION OF THE
TEST PRODUCTS (EXAMPLES 4 AND 5) OR OF THE VEHICLE ALONE
(PLACEBO: 10 ML OF A 50/50 (V/V) PEG-400/WATER MIXTURE)

| | | | Mean values (± standard deviation) of the durations of the states of consciousness (minutes) | | | | | Mean values (± standard deviation) of the latency times for the stages of consciousness (minutes) | | |
|---|---|---|---|---|---|---|---|---|---|---|
| | Dose ($\mu$mol/kg) | Route | Consciousness | Drowsiness | Slow-wave sleep S1 + S2 | P.S. | Total sleep | Drowsiness | Slow-wave sleep S1 | P.S. |
| Placebo | — | IV | 134.7 (16.5) | 11.3 (12.8) | 4.0 (4.3) | 0.0 (0.0) | 15.3 (16.5) | 88.8 (37.8) | 111.0 (47.1.9) | 117.3 (29.7) |
| Example 4 | 1.5 | IV | 115.4 (12.9) | 15.9 (9.0) | 16.3 (11.8) | 2.4 (4.1) | 34.6 (12.9) | 63.8 (28.8) | 84.8 (46.2) | 114.8 (35.1) |
| Example 5 | 1 | IV | 108.1 (22.9) | 15.8 (6.9) | 23.4 (17.4) | 2.6 (3.6) | 41.9 (22.9) | 51.7 (16.8) | 69.0 (24.2) | 110.7 (40.2) |

2. HYPNOTIC AND SEDATIVE ACTIVITIES IN CHICKS

The hypnotic and sedative effects of the derivatives, according to the invention, prepared above (the test results of which are given in Table II below) were compared with those of 3 reference products, diazepam, pentobarbital sodium and melatonin, as well as with 2 psychostimulant compounds with hallucinogenic properties: 10-methoxy harmalan and harmaline, which are 3,4-dihydro-$\beta$-carbolines, in 10 to 14-day-old chicks of chair label JA657 strain. The animals are subjected to programs of alternate lighting comprising 12 h of darkness (8.00 pm to 8.00 am) and 12 h of light (8.00 am to 8.00 pm) . The ambient temperature is 25° C. during the first week of rearing of the chicks and 22° C. from the second week onwards. During the day, the lighting is provided by a halogen lamp (300 W) placed 30 cm above the floor of the vivarium. During the tests, the live weights of the chicks ranged between 85 g and 120 g. The tests are carried out between 2.00 pm and 3.00 pm. The chicks are allotted, in groups of 3, in identical 30 cm×50 cm×30 cm vivariums. The test products are administered intramuscularly (IM) into the pectoralis major muscle, as a solution in an ethanol/PEG-400/distilled water mixture (25/50/25, V/V/V), at a rate of 0.2 ml of solution per 100 g of live weight. The doses administered for the test products (novel compounds of the invention and reference substances) range from 0.5 $\mu$mol to 2 $\mu$mol per 100 g of live weight. The placebo corresponds to 0.2 ml of the ethanol/PEG-400/distilled water mixture (25/50/25, V/V/V) per 100 g of live weight. Since ethanol is used as a solvent, its effect was compared beforehand with that of physiological saline (0.9% NaCl solute) or distilled water.

The solutions of the test products were prepared at the time of use by successive dilution in a stock solution, obtained from 5 to 20 $\mu$mol of accurately weighed product, to which were added 0.5 ml of pure ethanol and 1 ml of PEG-400, and then made up to 2 ml with 0.5 ml of distilled water for injectable preparations. Table II gives the results obtained after IM administration of doses of between 0.5 and 2 $\mu$mol of test products, dissolved in 0.2 ml of the ethanol/PEG-400/distilled water mixture (25/50/25, V/V/V) per 100 g of live weight. For each chick, the volume injected is adjusted, as a function of the actual live weight, to 0.2 ml per 100 g of live weight.

The parameters observed are the locomotor activity and the state of consciousness of the chicks for 2 h, i.e. the equivalent of 6 theoretical awake/asleep cycles for a chick of this age. They are recorded by video camera for 90 minutes, the first 30 minutes being the time for adaptation to the device.

Five stages of consciousness were defined:

Stage 1: active consciousness;

Stage 2: animal lying down, head held alert with tonicity, eyes open;

Stage 3: slightly sleepy, animal drowsy: eyes closed with intermittent opening, immobile posture not modified by stimulation;

Stage 4: deep sleep lying down: relaxation of the neck, characteristic posture with the head under the wing or hanging backward;

Stage 5: sleeping standing up: eyes closed, immobile, head hanging down (catatonic).

These five stages correspond approximately to the stages of consciousness and sleep defined in the examination of the electroencephalographic plots in this species. The correspondence is as follows:

Deep sleep lying down: Stage 4="slow wave sleep" (SWS)

Sleeping standing up="sleep-like state I" (SLSI).

The drowsy stage 3 might correspond to phases of paradoxal sleep, with agitation of the head, for example.

The chicks are observed by a trained observer with continuous video monitoring for at least one hour after the animals have woken up.

Two stimuli were used to confirm the observations of the behavior of the chicks at regular intervals:

the noise made by tapping a plastic object on the glass of the vivarium, comparable to that of the beak of a chick on the glass, corresponds to a moderate stimulus. It is carried out at each period of observation (i.e. every five minutes); and the presentation of a metal feed tray filled with the usual feed, left in the vivarium for 2 minutes. This is a powerful stimulus which calls on sight, hearing and smell. It is carried out every 15 minutes, i.e. at least 6 times in each test.

Wakefulness is defined by the appearance of the elaborate conscious behavior of searching for and consuming food or drink.

The Sleeping Time (ST) is defined by the sum of the durations of the phases of light sleep (Stage 3), deep sleep (Stage 4) and sleeping standing up (Stage 5). The Sedation Time, after waking up, corresponds to Stage 2.

The Falling-Asleep Time (FAT) is equal (to the nearest minute) to the time required to pass from the state of active consciousness (Stage 1) to an unconsciousness state (Stages 3, 4 and 5).

The hypnotic and sedative effects of the test products on the diurnal activity of 10- to 14-day-old chicks subjected to a program of permanent lighting from birth for 48 h, and then to a program of alternate lighting of 12 h of daylight (8.00 am–8.00 pm) and 12 h of darkness (8.00 pm–8.00 am) up to the test date, are given in Table II below. The tests are carried out during the day between 2.00 pm and 3.00 pm.

For each test product, several series of measurements were taken on batches of 3 animals, each value indicated being the mean for each batch of 3 chicks. When the number of batches is greater than 2, the figures indicated are the mean limit values observed.

administration of melatonin. The enzyme NAT is an acetylation enzyme. In the presence of the enzyme NAT in the pineal gland of the chick, the IM administration of melatonin induces a hypnotic effect of strong intensity (sleeping time of between 250 and 300 minutes for a dose equal to 1 μm of melatonin/100 g of live weight). Melatonin is thus the precursor of acetylated metabolites with direct hypnotic activity. The compounds described in the present invention are analogs of the hypnotic acetylated metabolites of melatonin.

Unlike melatonin, all the derivatives of the invention described above have direct hypnotic or sedative activities, which are independent of the time of administration, i.e. of the level of the enzyme N-acetyltransferase in the CNS.

The results obtained show, for the derivatives according to the invention, a hypnotic effect which is greater than that of the reference products (pentobarbital, melatonin) and equivalent to or even greater than that of diazepam.

The derivatives according to the invention are thus medicinal products that are particularly advantageous for treating conditions associated with disorders of melatonin activity. These derivatives can be used in particular as hypnotic or sedative medicinal products.

TABLE II

|  | Dose (μmol/100 g) | Dose (mg/kg) | FAT | ST | Sedation time |
|---|---|---|---|---|---|
| PLACEBO | (24 batches) |  | NA | 0 | 10–35 |
| MELATONIN | 0.5 | 1.16 | NA | 0 | ND |
|  | 1 (5 batches) | 2.32 | NA | 0 | 16–36 |
|  | 2 (5 batches) | 4.64 | NA | 0 | 47–105 |
| PENTOBARBITAL | 0.5 (3 batches) | 1.24 | NA | 0 | ND |
|  | 1 | 2.48 | 13 | 36 | ND |
| DIAZEPAM | 0.5 (4 batches) | 1.42 | 3–6 | 10–50 | ND |
|  | 1 (10 batches) | 2.85 | 2–7 | 24–70 | 17–20 |
|  | 2 (3 batches) | 5.69 | 2–5 | 81–100 | 14–15 |
| 10-METHOXYHARMALAN | 1.4 | 3 | NA | 0 | 0 |
| HARMALIN | 1.4 | 3 | NA | 0 | 0 |
| Example 6 | 2 | 5.44 | 15 | 33 | 27 |
| Example 1 | 2 | 5.40 | 10.5 | 30 | 35 |
| Example 4 | 1 | 2.98 | 13 | 30 | 47 |
| Example 9 | 1 | 3.12 | 7 | 36 | 44 |
| Example 5 | 0.87 | 3.12 | 10 | 36 | 44 |

NA: Not applicable, the animals remain conscious throughout the period of observation
FAT: Falling-asleep time = time required to pass from the state of active consciousness to an unconscious state
ST: Sleeping time = duration of the period of sleep from the time of falling asleep to the time of waking up
Sedation time: After waking up, period of inactivity = Stage 2 defined above
ND: Not determined Without wishing to be bound to any theory, the following argument may be put forward.

Under the conditions in which the test is carried out (administration times during the daylight phase of the animals between 2.00 pm and 3.00 pm), melatonin has no hypnotic activity.

By successively subjecting chicks to programs of alternating and permanent lighting, we have demonstrated experimentally that melatonin has no direct hypnotic activity which is intrinsic in its structure. Its hypnotic activity depends on the activity of the enzyme N-acetyltransferase (NAT) in the pineal gland of the chick at the time of

What is claimed is:
1. A pyrrolo[3,4-b]quinoline compound of formula I:

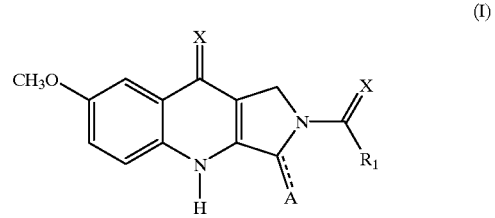

(I)

in which

X represents an oxygen atom or a sulfur atom,

represents a divalent radical of formula:

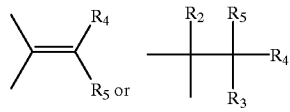

R₁ represents a lower alkyl radical containing from one to three carbon atoms, a lower cycloalkyl radical containing from three to six carbon atoms or R₁ represents a lower alkyl radical linked to R₄ to form a 6-atom ring containing 0, 1 or 2 unsaturations, R₂, R₃, R₄ and R₅ represent, independently of each other, a hydrogen atom, a lower alkyl group containing from one to three carbon atoms, a lower cycloalkyl group containing from three to six carbon atoms or a phenyl group, a racemic mixture, an enaritiomer, or mixtures thereof, or a pharmaceutically acceptable salt thereof.

2. Compound according to claim 1, in which R₁ represents a methyl, ethyl, n-propyl, isopropyl, or cyclopropyl group.

3. Compound according to claim 1, which is:

2-Acetyl-7-methoxy-3-methylene-9-oxo-1,3,4,9-tetrahydropyrrolo[3,4-b]quinoline,

2-Butyryl-7-methoxy-3-methylene-9-oxo-1 ,3,4,9-tetrahydropyrrolo[3,4-b]quinoline, 2-Cyclopropylcarbonyl-7-methoxy-3-methylene-9-oxo-1,3,4,9-tetrahydropyrrolo[3,4-b]quinoline, 1-Ethyl-9-methoxy-2,3,4,6,7,12-hexahydroindolizino[1,2-b]quinoline-4,7-dione, 9-Methoxy-1-phenyl-2,3,4,6,7,12-hexahydroindolizino [1,2-b]quinoline-4,7-dione, 2-Acetyl-7-methoxy-3-methyl-9-oxo-1,3,4,9-tetrahydropyrrolo[3,4-b]quinoline, 7-Methoxy-3-methyl-2-thioacetyl-9-thioxo-1,3,4,9-tetrahydropyrrolo[3,4-b]quinoline, 2-Acetyl-3,3-dimethyl7-methoxy-9-oxo-1,3,4,9-tetrahydropyrrolo[3,4-b]quinoline, 1-Ethyl-9-methoxy-1,2,3,4,6,7,12,12b-octahydroindolizino[1,2-b]quinoline-4,7-dithione, or 1,1-Diethyl-9-methoxy-1,2,3,4,6,7,12,12b-octahydroindolizino[1,2-b]quinoline-4,7-dithione.

4. Process for preparing a compound of formula I according to claim 1, wherein X represents an oxygen atom, which comprises oxidizing a compound of formula II

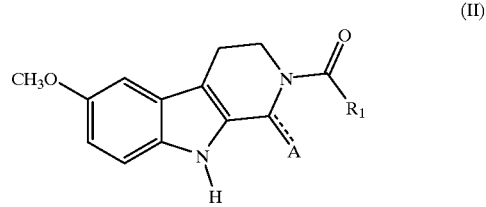

wherein R1 and A are as defined in claim 1, with oxygen in the presence of a base or with a periodate.

5. Process as claimed in claim 4, wherein the base is sodium hydride or potassium tert-butoxide.

6. Process as claimed in claims 4 or 5, wherein the compound of formula I is:

2-Acetyl-7-methoxy-3-methylene-9-oxo-1,3,4,9-tetrahydropyrrolo[3,4-b]quinoline,

2-Butyryl-7-methoxy-3-methylene-9-oxo-1,3,4,9tetrahydropyrrolo[3,4-b]quinoline,

2-Cyclopropylcarbonyl-7-methoxy-3-methylene-9-oxo-1,3,4,9-tetrahydropyrrolo[3,4-b]quinoline, 1-Ethyl-9-methoxy-2,3,4,6,7,12-hexahydroindolizino[1,2-b]quinoline-4,7-dione, 9-Methoxy-1-phenyl-2,3,4,6,7,12-hexahydroindolizino [1,2-b]quinoline-4,7-dione, 2-Acetyl-7-methoxy-3-methyl-9-oxo-1,3,4,9-tetrahydropyrrolo[3,4-b]quinoline, 2-Acetyl-3,3-dimethyl-7-methoxy-9-oxo-1,3,4,9-tetrahydropyrrolo[3,4-b]quinoline, 1-Ethyl-9-methoxy-1,2,3,4,6,7,12,12b-octahydroindolizino[1,2-b]quinoline-4,7-dithione, or 1,1-Diethyl-9-methoxy-1,12,3,4,6,7,12,12b-octahydroindolizino[1,2b]-quinoline-4,7-dithione.

7. Process for preparing a compound of formula I according to claim 1, wherein X represents a sulfur atom (X=S), which comprises reacting Lawesson's reagent, or phosphorus pentasulfide, with the corresponding oxygen derivative of formula I (X=O).

8. A composition comprising a compound of any one of claims 1 to 3 and a pharmaceutically acceptable carrier therefor.

9. A method of inducing a hypnotic activity, which comprises administering to an animal in need thereof a hypnotic activity-inducing amount of a compound of any one of claims 1 to 3.

10. A method of inducing a sedative activity, which comprises administering to an animal in need thereof a sedative activity-inducing amount of a compound of any one of claims 1 to 3.

* * * * *

UNITED STATES PATENT AND TRADEMARK OFFICE
CERTIFICATE OF CORRECTION

PATENT NO.   : 6,335,346 B1
DATED        : January 1, 2002
INVENTOR(S)  : Jean-Bernard Fourtillan et al.

It is certified that error appears in the above-identified patent and that said Letters Patent is hereby corrected as shown below:

Column 15,
Line 29, "enaritiomer" should read -- enantiomer --.
Line 37, "1 ,3,4,9-" should read -- 1,3,4,9- --.
Line 51, "dimethyl7" should read -- dimethyl-7 --.

Column 16,
Line 14, "R1" should read -- $R_1$ --.
Line 23, "9tetrahydropyrrolo" should read -- 9-tetrahydropyrrolo --.
Line 37, "1,12,3,4,6,7,12,12b-" should read -- 1,2,3,4,6,7,12,12b- --.

Signed and Sealed this

Seventh Day of May, 2002

Attest:

Attesting Officer

JAMES E. ROGAN
Director of the United States Patent and Trademark Office